United States Patent [19]

[11] 4,125,559

Scholz et al.

[45] Nov. 14, 1978

[54] MANUFACTURE OF ALKALI METAL SALTS OF ARABONIC ACID

[75] Inventors: Herbert Scholz, Ludwigshafen; Guenther Gotsmann, Frankenthal, both of Fed. Rep. of Germany

[73] Assignee: BASF Aktiengesellschaft, Ludwigshafen, Fed. Rep. of Germany

[21] Appl. No.: 798,336

[22] Filed: May 19, 1977

[30] Foreign Application Priority Data

Jun. 23, 1976 [DE] Fed. Rep. of Germany ....... 2628056

[51] Int. Cl.$^2$ ....................... C07C 51/26; C07C 59/17

[52] U.S. Cl. ..................................................... 562/531

[58] Field of Search ............................ 260/530 R, 528

[56] References Cited

U.S. PATENT DOCUMENTS

| | | | |
|---|---|---|---|
| 2,587,906 | 3/1952 | Schmidt | 260/528 |
| 2,922,698 | 1/1960 | Moser | 260/528 |

OTHER PUBLICATIONS

Bull. Soc. Chim. France, v. 1959, pp. 1353-1362.

*Primary Examiner*—Vivian Garner
*Attorney, Agent, or Firm*—Keil, Thompson & Shurtleff

[57] ABSTRACT

Alkali metal salts of arabonic acid are manufactured by oxidizing D-hexoses in the presence of alkali metal compounds under specific conditions in respect of temperature, pressure, reaction time, sequence of addition of the individual reactants and mixing.

The alkali metal salts of arabonic acid which may be manufactured by the process of the invention are valuable starting materials for the manufacture of vitamins, electro-coating assistants, crop protection agents and metal complexing agents.

8 Claims, No Drawings

MANUFACTURE OF ALKALI METAL SALTS OF ARABONIC ACID

The present invention relates to a new process for the manufacture of alkali metal salts of arabonic acid by oxidizing D-hexoses in the presence of alkali metal compounds under specific conditions in respect of temperature, pressure, reaction time, sequence of addition of the individual reactants and mixing.

Bull. Soc. Chim. France, volume 1959, pages 1,353–1,362, discloses the reaction of monosaccharides with oxygen in alkaline solution under atmospheric pressure to give alkali metal arabonates. The reaction temperature recommended in order to achieve yields of from 74 to 77 percent of theory are up to 45° C. in the case of D-glucose and up to 30° C. in the case of D-fructose. The oxygen is only added after dissolving the glucose in the alkali metal hydroxide solution. According to the description of the experiment, the process is based on an average speed of mixing of from 400 to 1,000 revolutions per minute. It is pointed out that specific reaction conditions must be observed since otherwise substantial amounts of degradation products of the hexoses, and discolorations of the reaction mixture and of the end product, are observed.

German Pat. No. 618,164 describes a corresponding reaction of D-glucose with potassium hydroxide solution and oxygen at from 35° to 40° C. under a gauge pressure of 1/10 atmosphere; the yield is 73 percent. According to the description of the experiment, the process is based on a speed of mixing of from 400 to 1,000 revolutions per minute.

East German Pat. No. 103,373 described, in its examples, a similar reaction at from 50° to 56° C., using air at atmospheric pressure. Stirrers are used to achieve mixing and speeds of from 400 to 600 revolutions, or more, per minute are preferred. A large part, or all, of the hexose, as well as the alkali, are introduced into the starting mixture before admitting oxygen.

All these processes give yields of only from 60 to 75 percent of theory.

German Pat. No. 815,644 describes the following method: an aqueous invert sugar solution is introduced into a glass tube and oxygen and potassium hydroxide solution are passed in simultaneously. During the reaction, the temperature rises to from 40° to 42° C. The reaction is carried out for 9 hours with oxygen or for 8 hours with air at atmospheric pressure. The patent does not describe any special mixing of the reaction batch. Drawing attention to the poor yields of 65 percent of theory (when using oxygen) or 53 percent of theory (when using air), the patent explains, and shows with the aid of numerous examples, that the reaction only gives higher yields, of up to 87 percent, in the presence of catalysts such as nitrobenzene.

We have found that alkali metal salts of arabonic acid, of the formula

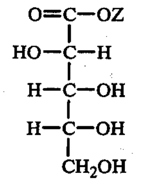

I where Z is an alkali metal atom, are obtained by reacting D-hexoses with oxygen and alkali metal compounds in aqueous solution, if one of the two starting materials D-hexose and alkali metal compound is heated, in aqueous solution, to above 30° C., oxygen is then passed into the solution, a pressure of from 1.5 to 40 bars is set up, finally the other of the two above starting materials is added and the reaction is carried out for at least 4.5 hours per mole, the starting materials used being D-glucose, D-fructose and/or D-mannose and the solution being mixed, during the reaction, at from 1,200 to 2,000 revolutions per minute.

When using D-glucose and potassium hydroxide solution, the reaction may be represented by the following equation:

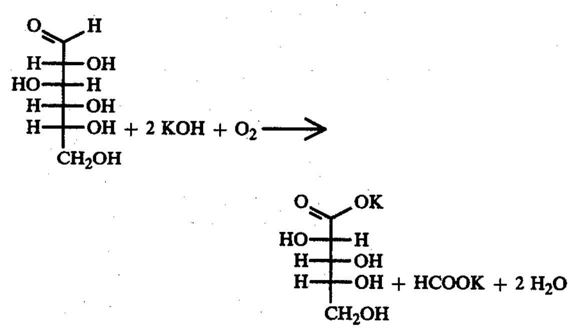

The invention is based on the observation that it is not one or a few parameters, such as temperature, time or a specific catalyst, but only a combination of numerous parameters, which are, under certain conditions, interrelated as regards their magnitude, are critical for optimum manufacture of the arabonates. Compared to the conventional processes, the process of the invention surprisingly gives alkali metal arabonates more simply and more economically, and in better yield and higher purity. It is not necessary to use catalysts.

D-Glucose, D-fructose, D-mannose and their mixtures, e.g. invert sugar, are used as D-hexoses. These monosaccharides can be present in various ring forms (pyranoses or furanoses) and as various diastereomers, for example, in the case of D-glucose, as α-D-glucopyranose and β-D-glcopyranose. The D-hexose is reacted with the alkali metal compound in a stoichiometric amount or in excess, preferably using an amount of from 2 to 5, especially from 2 to 3, equivalents of alkali metal compound per mole of D-hexose. Preferred alkali metal compounds are hydroxides, oxides and alcoholates, especially the sodium or potassium compounds. Examples of suitable compounds are potassium hydroxide, sodium hydroxide, sodium ethylene glycolate, sodium methylate, sodium propylate, sodium ethylate, sodium tripropylene glycolate and potassium tert.-butylate.

Oxygen is used as a mixture with inert gases, conveniently in the form of air, or, advantageously, by itself in stoichiometric amount or in excess; the use of amounts of from 1 to 20, preferably from 1 to 5, moles of $O_2$ per mole of D-hexose is advantageous. The reaction is carried out at above 30° C., advantageously at from 30° to 100° C., preferably from 40° to 60° C., under a pressure of from 1.5 to 40 bars, preferably from 18 to 25 bars, continuously or batchwise. The solvent used is water, advantageously in an amount of from 200 to 10,000, preferably from 200 to 3,000, percent by weight based on D-hexose. The water may be added separately or, advantageously, together with one of the starting materials, preferably in the form of either aqueous solutions of the alkali metal compound or aqueous solutions of hexose.

An important characteristic of the process, according to the invention, is the sequence of the various measures: 3 starting materials, namely oxygen, hexose and alkali metal compound, are reacted with one another in such a way that only one starting material is initially introduced in aqueous solution, oxygen or oxygen-containing gases, e.g. air, are then introduced and finally the third starting material, preferably again in aqueous solution, is added. It is advantageous to start with an aqueous solution of the alkali metal compound and to add the hexose, after introduction of oxygen, as the last starting material. The temperature is brought to above 30° C. even before introducing the oxygen. During the introduction of the oxygen and/or the last, i.e. third, starting material, and/or during the reaction, the initial temperature may still be changed, but it is advantageous to bring the solution to the final reaction temperature before introducing the oxygen. Advantageously, aqueous solutions containing from 1 to 50 percent by weight of the alkali metal compounds and/or aqueous solutions containing from 5 to 50 percent by weight of the hexoses are used.

Advantageously, the introduction of oxygen or of air is coupled with the adjustment of the pressure. The reaction time allowed after addition of the third starting material depends on the amount of starting hexose; after the latter has been added, the reaction is continued for at least 4.5 hours, advantageously for from 4.5 to 9 hours, and preferably for from 4.5 to 6 hours, per mole of D-hexose.

An essential feature of the process according to the invention is that the reaction mixture is thoroughly mixed during the entire reaction; speeds of stirring are from 1,200 to 2,000, especially from 1,500 to 2,000, revolutions per minute are used. In the case of mixing equipment without stirrers, equipment which introduces an amount of shearing energy corresponding to the above speed of stirring is preferred. Stirring devices which are extensively known can be used when applying the above mixing conditions. They include injectors, ball jets, vortex jets, turbine stirrers, mixing nozzles, Lechler mixing nozzles, paddle stirrers, anchor stirrers, bartype stirrers, propeller stirrers, Cramer stirrers, vibro-mixers, finger-type stirrers, crossbeam stirrers, gyratory stirrers, grid stirrers glat stirrers, spiral turbines, scoop stirrers, planetary stirrers, centrifugal gyratory stirrers, rotating atomizers, ejectors, triangular stirrers, hollow stirrers, tubular stirrers and impeller stirrers; impeller stirrers, centrifugal pumps and mixing nozzles are preferred. It is also possible to use equipment which permits thorough mixing, such as stirred kettles, stirred kettle cascades, flow tubes, air-lift type stirring units, homogenizing equipment, gyratory mixers, turbo-mixers, emulsifying centrifuges, ultrasonic tubes, flow mixers, rotating drums, chamber reactors, circulatory reactors, loop reactors, cellular reactors screw reactors, bubble columns, jet scrubbers, liquid ring pumps, ejector-type tubular reactors, thin film reactors and trickle columns; stirred kettle cascades, loop reactors, ejector-type reactors and trickle columns are preferred. Mixing can be started either after addition of the third starting material or after the reaction pressure has been set up or together with the introduction of oxygen; preferably, even the initial solution of the first starting material is mixed at the intensity or speed of revolution according to the invention, before oxygen is introduced, and mixing is maintained during the addition of the reactants and during the subsequent reaction.

The alkali metal salts of arabonic acid which can be manufactured by the process of the invention are valuable starting materials for the manufacture of vitamins, electro-coating assistants, crop protection agents and metal complexing agents. Thus, D-ribose, riboflavin and therefore a component of the vitamin B group can be manufactured from them. Regarding their use, reference may be made to the above publications and to Ullmanns Encyklopadie der technischen Chemie, volume 18, pages 187–194.

In the example which follows, parts are by weight.

EXAMPLE

A solution of 396.07 grams of KOH in 10,000 grams of water is introduced into a vertical tubular reactor of 2,000 mm length and 50 mm internal diameter which is packed with V2A steel Raschig rings of 6 mm diameter. The solution is heated to 45° C. and is mixed by means of a centrifugal pump, with a mixing effect corresponding to 1,950 revolutions per minute. 120 grams of oxygen are now introduced from the reactor top and the pressure is set to 20.5 bars. In the course of 5 minutes 1,000 grams of an aqueous solution containing 396.32 grams of D-glucose, monohydrate are added, using a metering pump, at the reactor top, to the alkaline solution, which is circulated by means of the centrifugal pump (1,950 revolutions per minute) in a downward direction via the reactor top. The solution is now mixed for 9 hours at 1,950 revolutions per minute and kept at 45° C. and 20.5 bars. It is then concentrated under 15 mbars until 500 grams of residue are left. This material is introduced into 6,000 grams of methanol, whilst stirring, whereupon crystalline potassium arabonate precipitates. Filtration gives 400.27 grams (98% of theory) of potassium arabonate of melting point 203–204° C. (with decomposition).

$^{13}$C-NMR spectrum [internal standard: sodium salt of 3-(trimethylsilyl)-propanesulphonic acid]

| Carbon atom | chemical shift (ppm) |
|---|---|
| 1 | 181.9 |
| 2 | 75.0 |
| 3 | 74.4 |
| 4 | 74.1 |
| 5 | 65.9 |

(CLERC, $^{13}$C-Kernresonanzspektroskopie (Akademische Verlagsgesellschaft Frankfurt am Main 1973), pages 35 and 37).

We claim:

1. A process for the manufacture of alkali metal salts of arabonic acid, of the formula

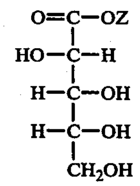

I where Z is an alkali metal atom, by reacting D-hexoses with oxygen and alkali metal compounds in aqueous solution, wherein one of the two starting materials D- hexose and alkali metal compound is heated, in aqueous solution, to a temperature of above 30° C. up to about 100° C., oxygen is then passed into the solution, a pressure of from 1.5 to 40 bars is set up, finally the other of the two above starting materials is added and the reaction is carried out for at least 4.5 hours per mole of D-hexose, the starting materials used being D-glucose, D-fructose and/or D-mannose and the solution being mixed, during the reaction, at from 1,200 or 2,000 revolutions per minute.

2. A process as set forth in claim 1, wherein the reaction is carried out with from 2 to 5 equivalents of alkali metal compound per mole of D-hexose.

3. A process as set forth in claim 1, wherein the reaction is carried out with from 1 to 20 moles of $O_2$ per mole of D-hexose.

4. A process as set forth in claim 1, wherein the reaction is carried out at from 40° to 60° C.

5. A process as set forth in claim 1, wherein the reaction is carried out under a pressure of from 18 to 25 bars.

6. A process as set forth in claim 1, wherein the reaction is carried out with from 200 to 10,000 percent by weight of water, based on D-hexose.

7. A process as claimed in claim 1, wherein the reaction is continued, after adding the third starting material, for from 4.5 to 9 hours per mole of D-hexose.

8. A process as claimed in claim 1, wherein the reaction is carried out using speeds of stirring of from 1,500 to 2,000 revolutions per minute.

* * * * *